United States Patent
Clayton

(10) Patent No.: US 10,137,033 B2
(45) Date of Patent: Nov. 27, 2018

(54) TORSIONAL MODE NEEDLE FOR PHACOEMULSIFICATION

(71) Applicant: Moog Inc., East Aurora, NY (US)

(72) Inventor: Larry Clayton, Farmington, UT (US)

(73) Assignee: Moog Inc., Elma, NY (US)

( * ) Notice: Subject to any disclaimer, the term of this patent is extended or adjusted under 35 U.S.C. 154(b) by 228 days.

(21) Appl. No.: 14/687,466

(22) Filed: Apr. 15, 2015

(65) Prior Publication Data

US 2016/0302816 A1    Oct. 20, 2016

(51) Int. Cl.
*A61F 9/007* (2006.01)
*G06F 17/50* (2006.01)
*A61B 17/00* (2006.01)
*A61B 17/32* (2006.01)

(52) U.S. Cl.
CPC ...... *A61F 9/00745* (2013.01); *G06F 17/5018* (2013.01); *A61B 2017/00725* (2013.01); *A61B 2017/320098* (2017.08)

(58) Field of Classification Search
CPC ............... A61B 2017/320096; A61F 9/00745
See application file for complete search history.

(56) References Cited

U.S. PATENT DOCUMENTS

| | | | |
|---|---|---|---|
| 5,718,676 A | 2/1998 | Barrett | |
| 5,935,096 A | 8/1999 | Barrett | |
| 6,283,974 B1* | 9/2001 | Alexander | .......... A61F 9/00745 604/22 |
| 6,984,220 B2 | 1/2006 | Wuchinich | |
| 8,395,299 B2 | 3/2013 | Bromfield | |
| 8,610,334 B2 | 12/2013 | Bromfield | |
| 2001/0011176 A1 | 8/2001 | Boukhny | |
| 2003/0125620 A1* | 7/2003 | Satou | ........................ B06B 3/00 600/437 |
| 2006/0047254 A1 | 3/2006 | Akahoshi | |
| 2009/0137971 A1 | 5/2009 | Akahoshi | |
| 2011/0208114 A1 | 8/2011 | Morlet | |
| 2012/0072197 A1* | 3/2012 | Ovchinnikov | ...... A61F 9/00745 703/11 |
| 2012/0293044 A1 | 11/2012 | Bromfield | |
| 2014/0074013 A1* | 3/2014 | McCary | ............. A61F 9/00745 604/22 |

OTHER PUBLICATIONS

Rozenberg, L.D., editor, Sources of High-Intensity Ultrasound, 1969, vol. 2, Chapter 5, pp. 173-183, Plenum Press, New York, U.S.A.

* cited by examiner

*Primary Examiner* — Alexander Orkin
(74) *Attorney, Agent, or Firm* — Hodgson Russ LLP

(57) ABSTRACT

A phacoemsulsification needle for use with an ultrasonic handpiece in performing cataract surgery has a plurality of external grooves along its shaft. The external grooves are configured to convert longitudinal drive motion delivered by the handpiece at the base of the needle into torsional motion at the needle tip. The torsional motion at the needle tip has a magnitude greater than the magnitude of the longitudinal drive motion at the base, i.e. the longitudinal to torsional gain is greater than one. The grooves may be helical grooves, wherein the groove configuration is defined by a set of groove parameters including a helical pitch of the grooves, a width of the grooves, a depth of the grooves, an axial length of the grooves, and a total number of grooves.

10 Claims, 9 Drawing Sheets

SIX GROOVES

FIVE GROOVES

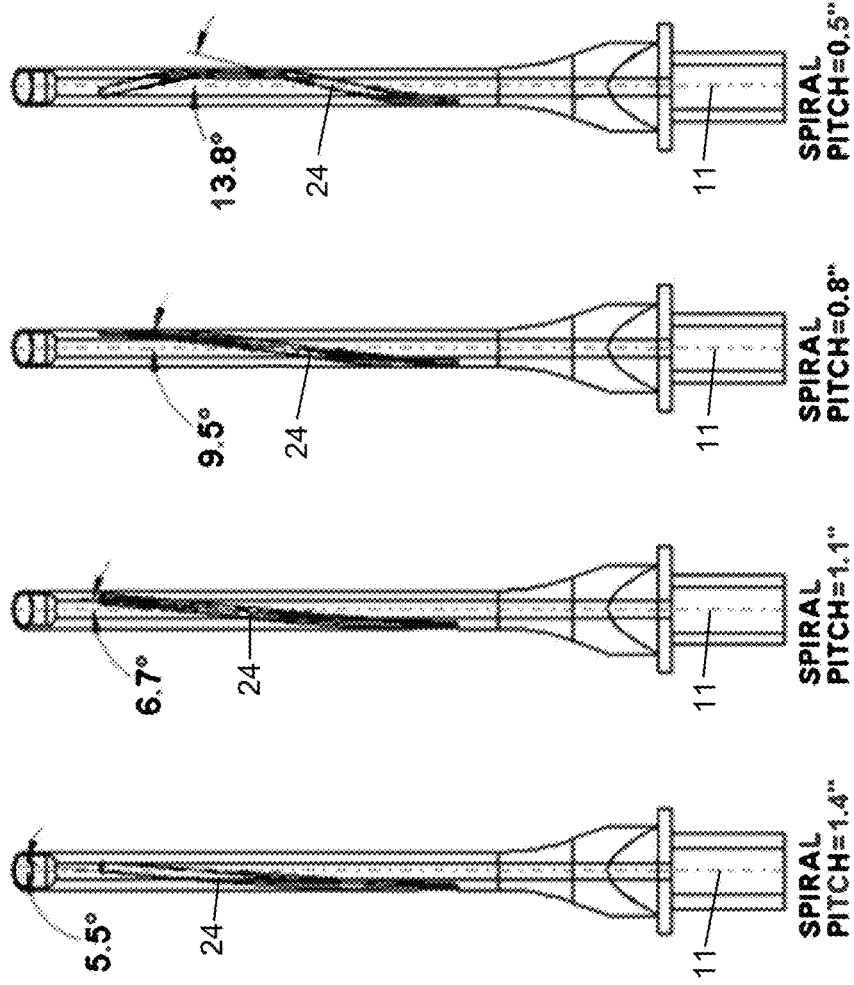

TORSIONAL MODE NEEDLE FOR PHACOEMULSIFICATION

FIELD OF THE INVENTION

The present invention relates generally to ultrasonic handpieces and needles used, for example, in cataract surgery to emulsify the internal lens and aspirate the lens from the eye.

BACKGROUND OF THE INVENTION

Historically, cataract surgery has been performed using ultrasonic handpieces providing a longitudinal or "jackhammer" like motion at a tip of a needle received by the handpiece. High-powered longitudinal mode ultrasonic handpieces used in cataract surgery typically consist of the components depicted in FIG. 1. The surgical needle threads into a stepped horn which is ultrasonically driven by a stack of piezoelectric ceramic elements. A spacer is located behind the stack of ceramic elements. A rear mass with a mount, isolation tube and Luer connector threads onto a center bolt which passes through the stack. When torqued, the rear mass applies a compressive pre-load to the stack. A lumen for aspiration of fragmented cataract tissue passes through the needle into the horn, through the center bolt and into the rear mass, exiting the Luer connector and passing into a flexible tube which is attached to a pump. O-ring bore seals, one located behind the horn step and the other in the rear mount, provide a water tight barrier for the handpiece inside its housing.

With longitudinal mode handpieces, cutting only occurs for the half of the oscillation cycle during which the needle tip advances toward the cataract. For the half of the cycle during which the needle tip moves away from the cataract, the needle tip is not cutting, but energy is required and heat is generated throughout the entire cycle. As a result, cutting efficiency is not optimized and cutting time is increased.

Torsional mode phacoemulsification was introduced by Alcon, Inc. in 2006 in the form of the OZil® handpiece depicted in FIG. 2. The OZil® handpiece delivers both longitudinal and torsional motion to the needle, which, depending upon the tip geometry, cuts in either a rotating or transverse shearing motion. Longitudinal vibration generated by the stack is partially converted to torsional motion by a torsional spring integrally machined into the horn of the OZil® handpiece depicted in FIG. 2. A bent tip needle with a Kelman configuration amplifies the shaft torsion through a side-to-side pivoting motion at the tip while a needle with a straight or flared tip cuts with a rotational motion amplified by the distance from the center of the needle to the outermost cutting edge of the tip.

When the needle tip is moving transversely or rotationally in torsional mode, more edge is applied to cutting as opposed to repulsing the cataract, and the needle tip maintains contact with the cataract throughout the cycle to cut more efficiently than purely longitudinal mode handpieces.

An improvement on the OZil® handpiece is described in U.S. Pat. No. 8,395,299 (Bromfield). Unlike the OZil® handpiece, in which the spring partially converting longitudinal motion to torsional motion is integral with the horn, the Bromfield design incorporates the spring into the handpiece as a discrete component. This significantly enhances design flexibility by facilitating alternative configurations and alternative spring materials to achieve different performance objectives.

U.S. Pat. No. 5,935,096 (Barrett) discloses needles used for emulsifying and removing the eyes lens during cataract surgery. A sleeve is arranged to surround the needle, and irrigant (i.e. liquid coolant) is fed to the surgical site through the space between the inner wall of the sleeve and the outer surface of the needle to reduce the risk of heat damage to the eye. In various embodiments, grooves are formed in the outer surface of the needle to provide channels by which the irrigant flows to the surgical site even when the entry wound compresses the sleeve against the outer surface of the needle. The shape, number and dimensions of the grooves do not matter so long as they provide a pathway for the irrigant to reach the internal chamber of the eye when the sleeve is compressed. In one embodiment shown at FIG. 5, the needle has multiple parallel helical grooves extending along the length of the outer surface of the needle shaft. The specific dimensions of the helical grooves are not discussed, and conversion of longitudinal drive motion to torsional motion at the needle tip is not described.

U.S. Patent Application Publication No. 2006/0047254 A1 (Akahoshi). also discloses several different embodiments of a needle used for emulsifying and removing the eye lens during cataract surgery. One of the embodiments, illustrated at FIG. 9a, has multiple parallel helical grooves extending along the length of the external surface of the needle shaft. Similar to the Barrett patent discussed above, the Akahoshi patent application is concerned with prevention of overheating at the surgical wound site. The Akahoshi patent application, unlike the Barrett patent, seeks to reduce heat generation without an outer sleeve (although a sleeve may also be used). Akahoshi discloses that from three to as many as five parallel helical grooves having a pitch angle in a range from 3° to 30° will generate a "reflux" flow of irrigant when the needle is used without a sleeve. The disclosure suggests that reflux is aided by using rounded or semicircular grooves that smoothly diminish in depth approaching the both ends of the groove. The specific dimensions of the helical grooves are not discussed, and conversion of longitudinal drive motion to torsional motion at the needle tip is not described.

SUMMARY OF THE INVENTION

It is an objective of the current invention to generate both longitudinal and torsional motion at the needle tip from an ultrasonic handpiece without incorporating torsional springs either integral to the horn as in FIG. 2 or as a discrete additional component according to Bromfield.

It is further an objective of the invention to provide handpieces already incorporating a torsional spring with increased torsional motion at the needle tip to improve lens cutting efficiency during cataract surgery.

A phacoemulsification needle is provided for use with an ultrasonic handpiece. The needle comprises a base adapted for removable attachment to the handpiece, and an elongated shaft extending from the base along a longitudinal axis, the shaft terminating at a distal tip having a cutting edge. The base and the shaft including an aspiration lumen passing therethrough. The shaft further includes a plurality of external grooves extending in a longitudinal direction of the shaft.

In accordance with the present invention, the plurality of grooves have a configuration that converts oscillatory longitudinal drive motion applied at the base of the needle to torsional motion at the tip of the needle. The torsional motion has a fundamental torsional mode frequency and a torsional mode magnitude, and is characterized by the torsional mode magnitude being greater than the longitudinal drive magnitude. In other words, a longitudinal to torsional gain provided by the needle is greater than one. The external grooves may be helical grooves extending in the longitudinal direction of the needle shaft. The desired longitudinal to torsional gain may be achieved by adjusting configuration parameters of the grooves, which may include a helical pitch of the grooves, a depth of the grooves, an axial length of the grooves, and a total number of grooves.

The invention is also embodied by a phacoemulsification system comprising an ultrasonic handpiece operable to provide at least an oscillatory longitudinal drive motion having a longitudinal drive frequency and a longitudinal drive magnitude, and a phacoemulsification needle, as summarized above, that is removably attached to the handpiece. In a particular embodiment, the handpiece may be operable to provide a combined longitudinal and torsional drive motion, and the needle increases torsional motion at the needle tip.

The invention is further embodied by a method of tuning a phacoemulsification system having an ultrasonic handpiece and an elongated needle removably attached to the handpiece. The method generally comprises the steps of digitally modelling the needle, providing a longitudinal drive frequency and a longitudinal drive magnitude of longitudinal drive motion to be supplied to the needle by the handpiece, and simulating harmonic response of the needle to application of the longitudinal drive motion to ascertain an expected fundamental torsional mode frequency and an expected torsional mode magnitude occurring at a distal tip of the needle. The digital model of the needle includes geometric dimensions and material of the needle. The geometric dimensions of the needle define a plurality of external helical grooves extending in a longitudinal direction of the needle. The method comprises adjusting at least one of the following parameters of the plurality of grooves until the expected torsional mode magnitude is greater than the longitudinal drive magnitude: (i) helical pitch of the grooves, (ii) depth of the grooves, (iii) axial length of the grooves, and (iv) total number of grooves.

The present invention enables a traditional longitudinal mode handpiece to be used to perform torsional mode cataract surgery, and enables selection of desired torsional mode operating characteristics by selecting a needle having a particular groove configuration from a plurality of needles having different respective groove configurations.

BRIEF DESCRIPTION OF THE DRAWINGS

The nature and mode of operation of the present invention will now be more fully described in the following detailed description of the invention taken with the accompanying drawing figures, in which:

FIGS. 5A-5D are side views of phacoemulsification needles embodying the present invention, wherein a helical pitch (i.e. spiral pitch) and groove angle are altered to provide different groove configurations;

DETAILED DESCRIPTION OF THE INVENTION

Figure 1:
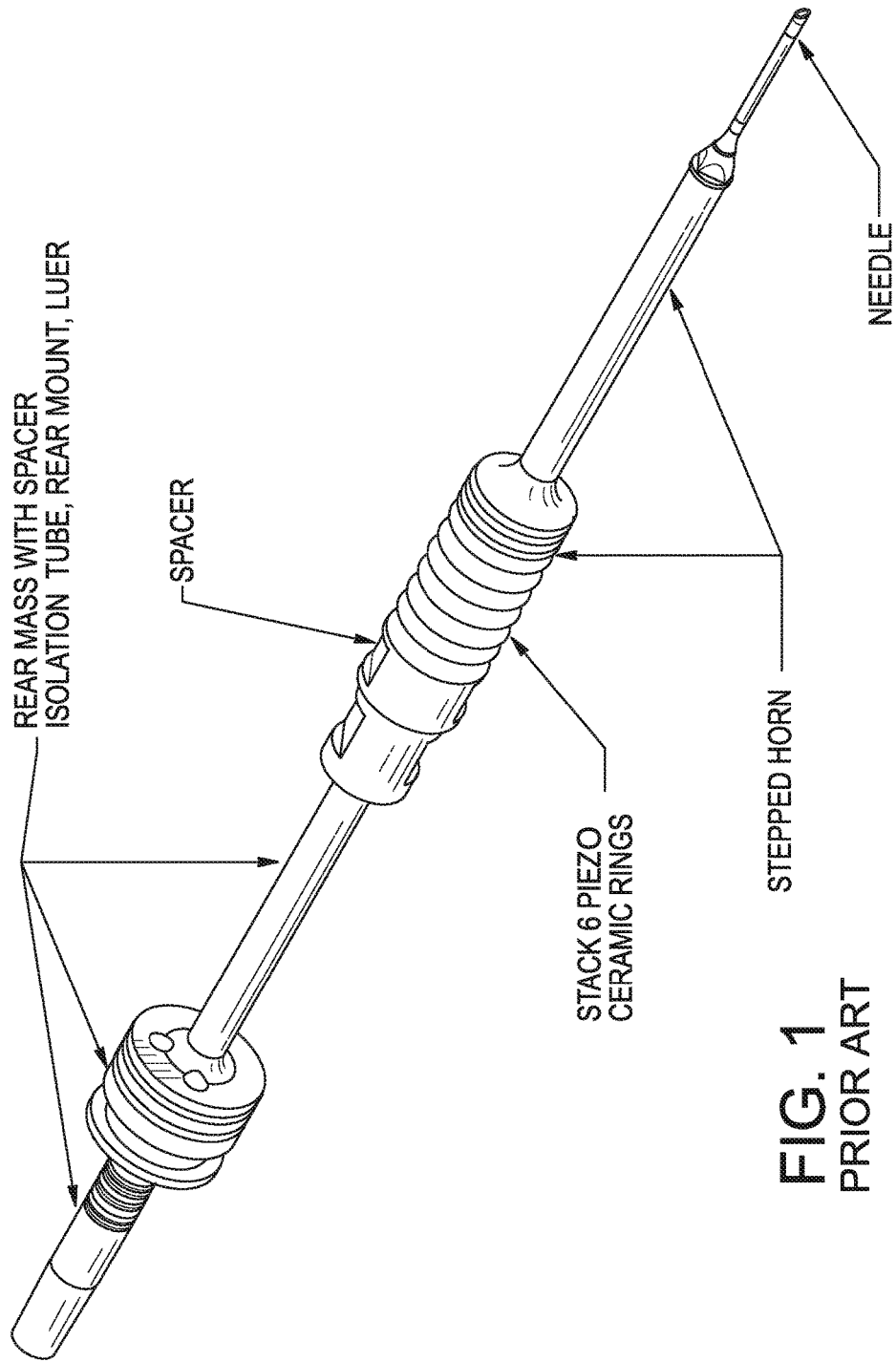
FIG. 1 is a perspective view of a longitudinal mode ultrasonic handpiece of the prior art.
Figure 2:
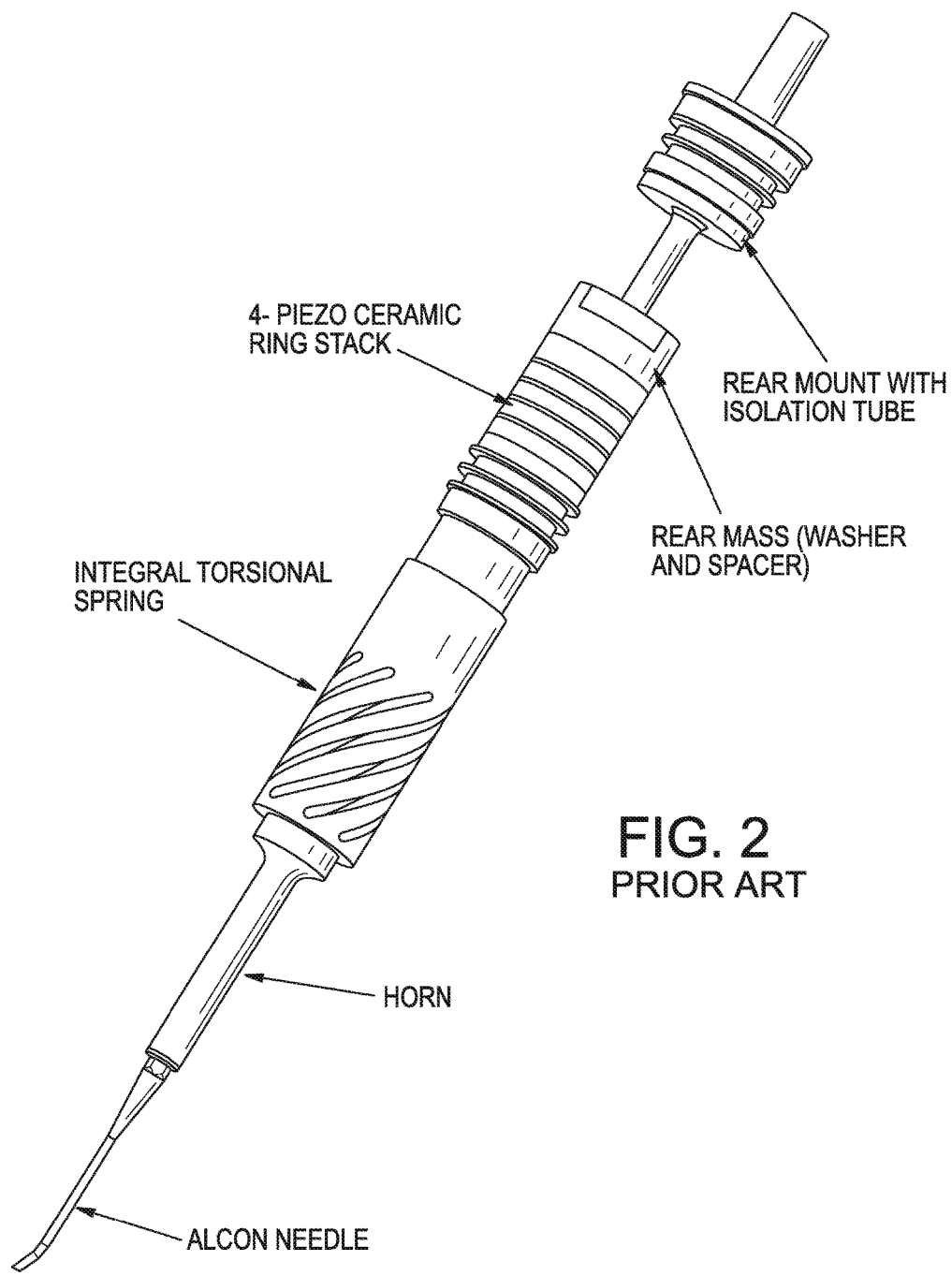
FIG. 2 is a perspective view of a combined longitudinal mode and torsional mode ultrasonic handpiece of the prior art.
Figure 3:
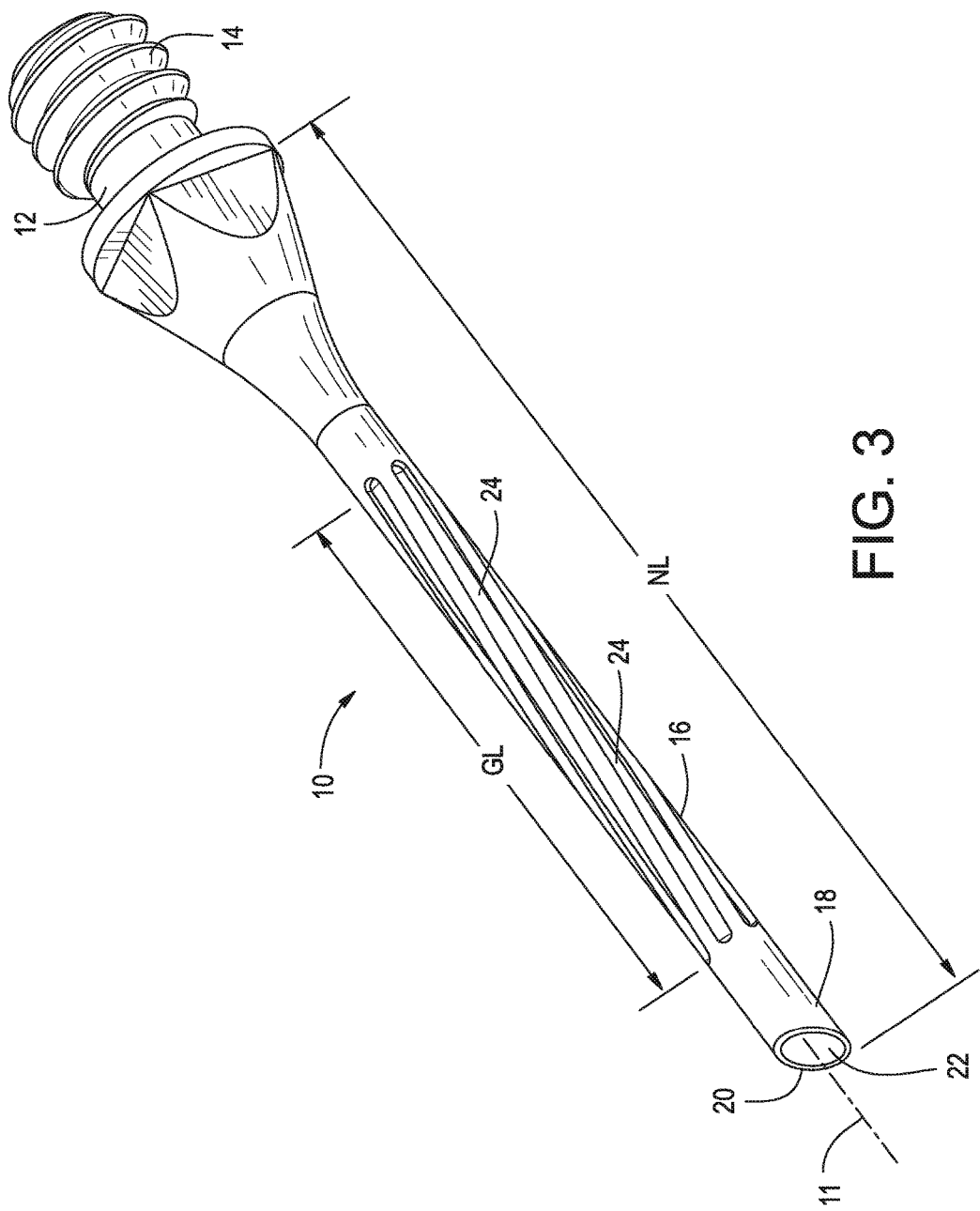
FIG. 3 is a perspective view of a phacoemulsification needle formed in accordance with an embodiment of the present invention, illustrating a groove length (GL) dimension.
Figure 4:
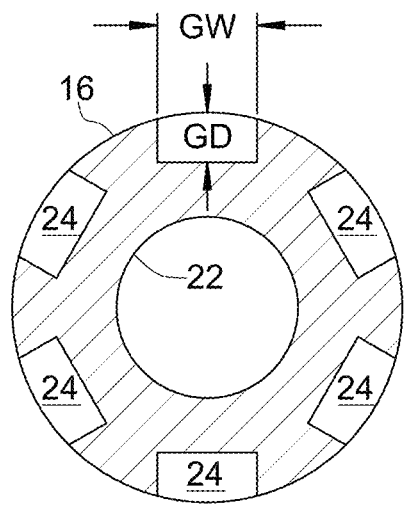
FIG. 4 is an enlarged transverse cross-sectional view through a shaft of the needle shown in FIG. 3, illustrating groove width (GW) and groove depth (GD) dimensions.

FIGS. 3 and 4 illustrate a phacoemulsification needle 10 formed in accordance with an embodiment of the present invention. Needle 10 is designed for attachment to an ultrasonic handpiece operable to drive the needle back-and-forth in opposite longitudinal directions of the needle at a longitudinal drive frequency and a longitudinal drive magnitude. Needle 10 comprises a base 12 adapted for removable attachment to the handpiece, for example by providing threads 14, and an elongated shaft 16 extending from base 12 along a longitudinal axis 11. Shaft 16 terminates at a distal tip 18 having a cutting edge 20. Tip 18 may be chamfered, for example at a 30° chamfer angle relative to axis 11. Base 12 and shaft 16 include an aspiration lumen 22 passing therethrough along axis 11. Shaft 16 further includes a plurality of external grooves 24 extending in the longitudinal direction of the shaft. Grooves 24 may be configured as helical grooves extending in the longitudinal direction of shaft 16. Needle 10 may be made of titanium alloy Ti-6Al-4V providing biocompatibility, good spring and fatigue characteristics, and a high stiffness to density ratio. Of course, other suitable materials may be used without straying from the present invention.

Grooves 24 are formed in an outer cylindrical surface of shaft 16 and may be configured as a plurality of parallel helixes around the circumference of the needle shaft. Grooves 24 may be produced in a manner similar to straight grooves by rotating needle 10 as the grooves are being formed. As will be described in detail below, the plurality of grooves 24 have a configuration that converts oscillatory longitudinal drive motion applied at base 12 of needle 10 to both longitudinal and torsional motion at tip 18 of the needle. The torsional motion at tip 18 has a fundamental torsional mode frequency and a torsional mode magnitude. In accordance with the present invention, grooves 24 are configured such that the torsional mode magnitude produced at tip 18 is greater than the longitudinal drive magnitude imparted to needle 10 at base 12 by the ultrasonic handpiece. In other words, grooves 24 are configured such that the longitudinal to torsional gain ("L-T gain"), defined as the torsional mode magnitude at tip 18 divided by the longitudinal drive magnitude, is greater than one. This is accomplished without a torsional spring or some other mechanism in the handpiece which converts longitudinal motion to torsional motion.

Grooves 24 may be spaced at regular angular intervals about axis 11. In the illustrated embodiment, the configuration of grooves 24 is defined by various parameters, including a helical pitch (also referred to as spiral pitch) of the grooves, a depth of the grooves GD, an axial length of the grooves GL, and a total number of grooves. Computer modeling and simulation may be used to determine suitable values of the groove configuration parameters that will result in a torsional mode magnitude that is greater than the longitudinal drive magnitude.

Performance characteristics and advantages of the needle depicted in FIGS. 3 and 4 will become evident with simulation of various needle and groove geometric configurations. Finite element analytical techniques were used to simulate needle dynamics for the various geometric configurations. The analytical approach used to simulate needle performance begins with the generation of three-dimensional solid and finite element models of the needles. The solid models may be created in a three-dimensional CAD modelling software application and then imported into a suitable finite element analysis (FEA) software application capable of performing dynamic FEA structural analysis. By way of non-limiting example, the models may be stored as Parasolid files and imported into ANSYS Workbench Version 15.0, which creates corresponding finite element models of the needles. The finite element models may include a mesh of quadratic hexahedral elements for computational accuracy, assignment of the needle material properties (e.g. Ti-6Al-4V), and application of the boundary conditions. Dynamic simulations may be performed by the software for the needle geometries in air, neglecting the damping effects of irrigation and aspiration flows as well as tip loading during testing and actual surgical procedures.

Modal analysis was performed for each needle and multiple groove configuration to compute resonant mode shapes and corresponding resonant frequencies. Modes of particular interest are the fundamental half wavelength torsional and longitudinal modes for the needle configurations. The degree to which the needle with multiple grooves converts longitudinal to torsional motion partially depends upon how close the operating drive frequency of the longitudinal mode of the handpiece is to the fundamental torsional mode frequency of the needle. Maximum displacements for both longitudinal and torsional modes occur at the tip 18 of the needle, and minimum displacements occur at the transition from base 12 to shaft 16.

Harmonic response analysis may be performed for each needle configuration to simulate the driven response at a particular frequency. The needle response to longitudinal excitation is simulated by an enforced longitudinal displacement at the base of the needle. For purposes of demonstration the longitudinal displacement magnitude used for this analysis is 0.0001 m. Any reasonable magnitude could be used to compute the L-T gain at needle tip 18 for a given longitudinal motion input at needle base 12. A longitudinal drive frequency of 41.5 KHz was used in the present analysis for the longitudinal mode of operation representative of handpieces used for cataract surgery. Again, any reasonable frequency typical of the longitudinal mode of operation for handpieces used in cataract surgery could be selected. Results from the harmonic response analyses include the L-T gain, the longitudinal to longitudinal gain ("L-L gain") defined as the longitudinal mode magnitude at tip 18 divided by longitudinal drive magnitude, and the torsional to longitudinal ratio ("T-L ratio") defined as the torsional mode magnitude at tip 18 divided by the longitudinal mode magnitude at tip 18. Maximum nodal displacements for the cutting edge 20 at tip 18 were obtained for the longitudinal direction and for torsional rotation about the longitudinal axis 11 of the needle. These displacements were used to compute the L-T gain, the L-L gain, and the T-L ratio.

Simulations were performed for needle configurations wherein the basic overall dimensions of the needle remained constant, while groove-related parameters including groove helical pitch, groove axial length, groove depth, and total number of grooves were varied in a controlled manner to determine how the parameters influence harmonic response, and what values of the groove configuration parameters may be suitable to achieve an L-T gain greater than one. For embodiments described herein, the overall dimensions of the modelled needle 10 were chosen to be equivalent to the dimensions of an existing Stellaris® needle sold by Bausch & Lomb Incorporated having straight grooves (i.e. grooves parallel to axis 11). The needle length NL was 18.796 mm (0.740 inches), the outer diameter of needle shaft 16 was 1.092 mm (0.043 inches), and the inner diameter of needle shaft 16 was 0.495 mm (0.020 inches). The number of grooves 24 was initially chosen to be the same as the number of straight grooves in the Stellaris® needle, namely six total grooves. The axial groove length GL, groove width GW, and groove depth GD were also initially chosen to be the same as those of the straight grooves in the Stellaris® needle, namely a groove length GL of 10.160 mm (0.400 inches), a groove width GW of 0.279 mm (0.011 inches), and groove depth GD of 0.140 mm (0.0055 inches).

Figure 6:
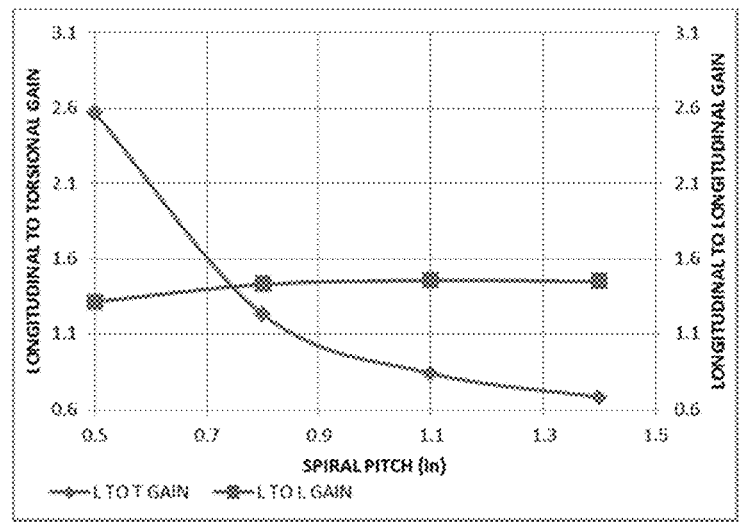
FIG. 6 is a graph showing variation of longitudinal to torsional gain and longitudinal to longitudinal gain as a function of the helical pitch of the grooves.
Figure 7:
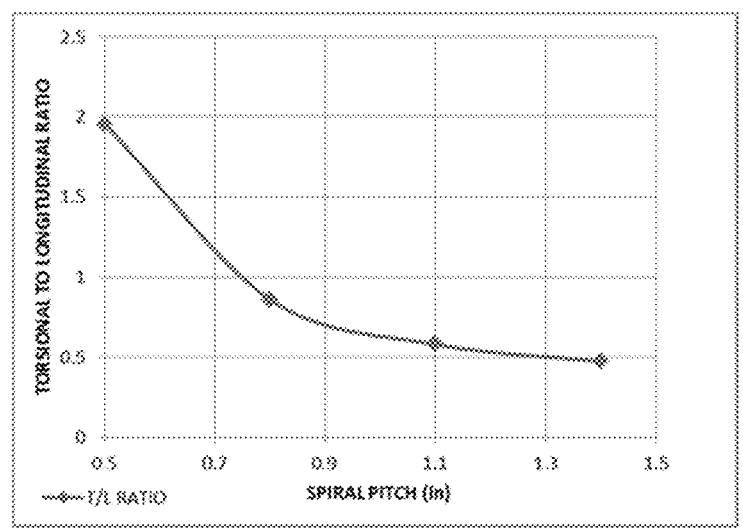
FIG. 7 is a graph showing variation of torsional to longitudinal ratio as a function of the helical pitch of the grooves.
Figure 8:
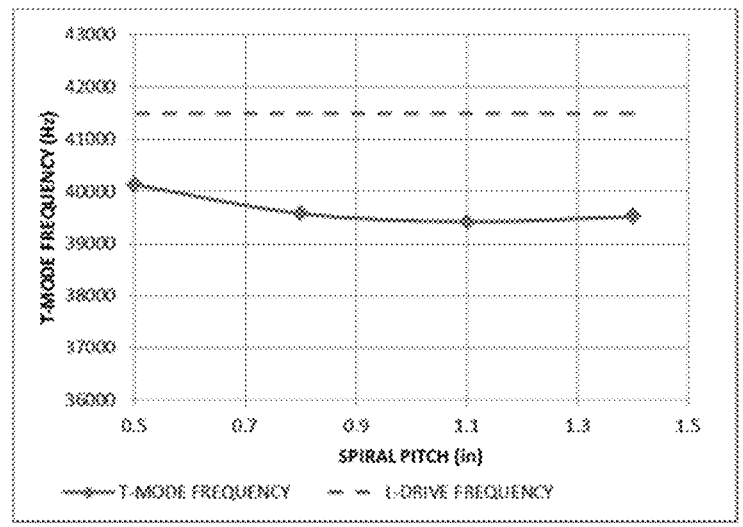
FIG. 8 is a graph showing variation of torsional mode frequency as a function of the helical pitch of the grooves.

In one set of simulations, the helical pitch parameter was varied as shown in FIGS. 5A-5D. Helical pitches of 1.4 inches, 1.1 inches, 0.8 inches, and 0.5 inches were chosen. As will be understood, varying the helical pitch also varies the angle of the groove centerline with respect to the longitudinal axis 11 of the needle. In the present example, a helical pitch of 1.4 inches corresponds to a groove angle of 5.5°, a helical pitch of 1.1 inches corresponds to a groove angle of 6.7°, a helical pitch of 0.8 inches corresponds to a groove angle of 9.5°, and a helical pitch of 0.5 inches corresponds to a groove angle of 13.8°. Modal and harmonic response analyses were performed for needle 10 with the varying helical pitches depicted in FIGS. 5A-5D for six equally spaced grooves 24 having the groove dimensions mentioned above. A longitudinal drive frequency of 41.5 KHz was used. Plots of L-T gain and L-L gain as a function of helical pitch appear in FIG. 6. The T-L ratio at tip 18 is plotted in FIG. 7 as a function of helical pitch. The variation in the torsional mode resonant frequency with helical pitch is plotted in FIG. 8.

As may be seen, longitudinal motion at the base 12 of the needle 10 is increasingly converted to torsional motion at the tip 18 as the helical pitch decreases and the groove angle increases reaching a maximum L-T gain of 2.6 for a helical pitch of 0.5 inches. While the L-T gain increases, the L-L gain remains relatively unchanged, and just below a helical pitch of about 0.75 inches the L-T gain surpasses the L-L gain. The increasing L-T gain and relatively constant L-L gain with helical pitch is reflected in a T-L ratio which progressively increases as the helical pitch decreases, reaching a maximum of approximately 2 for a helical pitch of 0.5 inches. The longitudinal base motion is increasingly converted to torsional motion while the difference between the drive frequency and torsional mode frequency for the changes in helical pitch exceeds 1300 Hz. Therefore, significant increases in L-T gain and T-L ratio may be achieved without the torsional resonant frequency and the drive frequency being closely matched.

Figure 9:
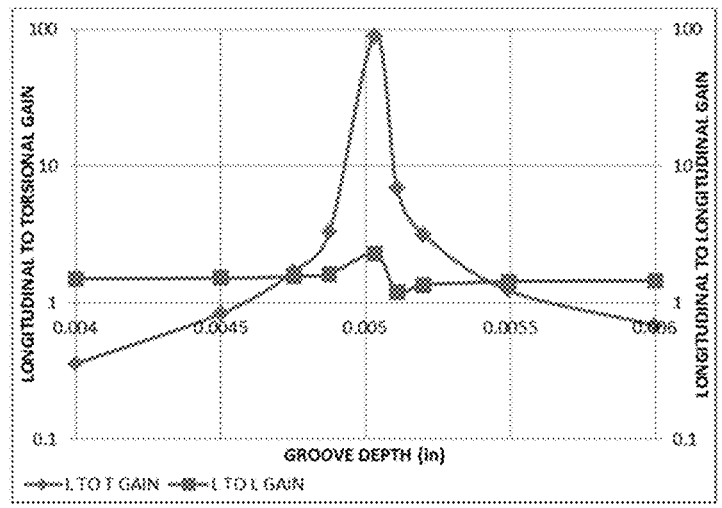
FIG. 9 is a graph showing variation of longitudinal to torsional gain and longitudinal to longitudinal gain as a function of groove depth.
Figure 10:
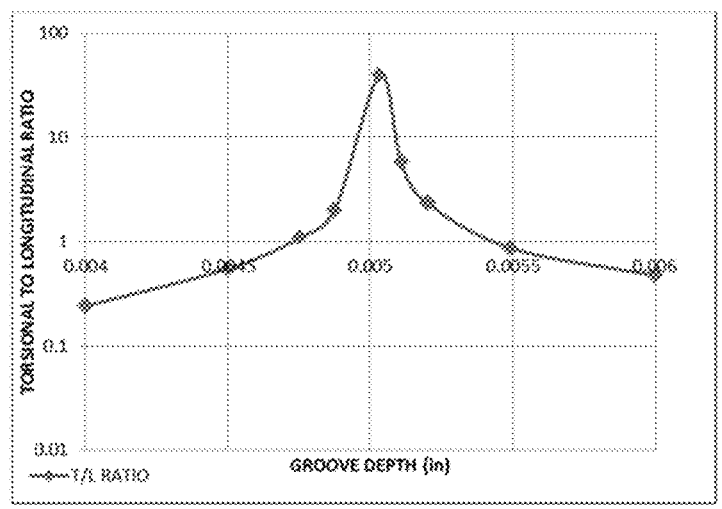
FIG. 10 is a graph showing variation of torsional to longitudinal ratio as a function of groove depth.
Figure 11:
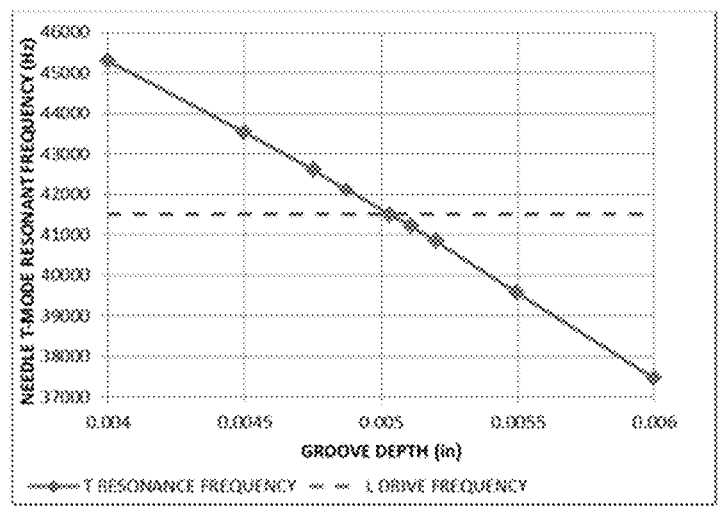
FIG. 11 is a graph showing variation of torsional mode frequency as a function of groove depth.

Another series of simulations was performed using a constant helical pitch of 0.8 inches while varying the groove depth GD of the six helical grooves 24; other groove dimensions were held constant. An objective of this series of simulations was to match the resonant frequency of the fundamental torsional mode of needle 10 to the longitudinal drive frequency of 41.5 KHz. The L-T gain and L-L gain are plotted in FIG. 9 for variations in the groove depth. FIGS. 10 and 11 depict variations in T-L ratio and torsional mode resonant frequency as a function of groove depth. The L-T gain in FIG. 9 and T-L ratio in FIG. 10 exhibit a peak value corresponding to a groove depth GD of roughly 0.005 inches, for which the longitudinal drive frequency and the torsional mode resonant frequency are closely matched as seen in FIG. 11. This indicates that the needle operates most efficiently converting longitudinal input motion at the base to torsional output motion at the tip when the longitudinal drive frequency matches the torsional resonant frequency of the needle. It is an advantage of the present invention that the torsional resonant frequencies for the various combinations of needle and groove dimensions and material properties produce torsional mode resonant frequencies which are close to the operating drive frequencies of handpieces with needles used for longitudinal mode cataract surgery, which typically range from 38 KHz to 44 KHz. It is a further advantage of the invention that the torsional resonant frequency of the needle may be readily adjusted within this range by varying the groove depth GD of grooves 24 as shown in FIG. 11. While optimum linear to torsional conversion will occur when the drive frequency substantially matches the needle torsional resonant frequency, FIGS. 9-11 indicate that significant L-T gains and T-L ratios may be achieved even when these frequencies are not ideally matched. It is noted that the simulations were performed assuming the needle to be in air, i.e. without damping or losses arising from tip loading, aspiration and irrigation flows. Damping will decrease the L-T gain for the needle. High stresses generated in the needle are also inherent with high gain. Fatigue will limit the degree to which longitudinal to torsional conversion for the needle may be optimized. While damping will reduce L-T gain, it will also reduce stress and improve needle fatigue life. It may be advantageous to drive the needle at a longitudinal drive frequency slightly off the peak frequency at torsional resonance to achieve a desired balance of high L-T gain and long fatigue life. In addition, the needle is changeable and may be replaced following each surgery to achieve high L-T gain and avoid fatigue failure.

Figure 12:
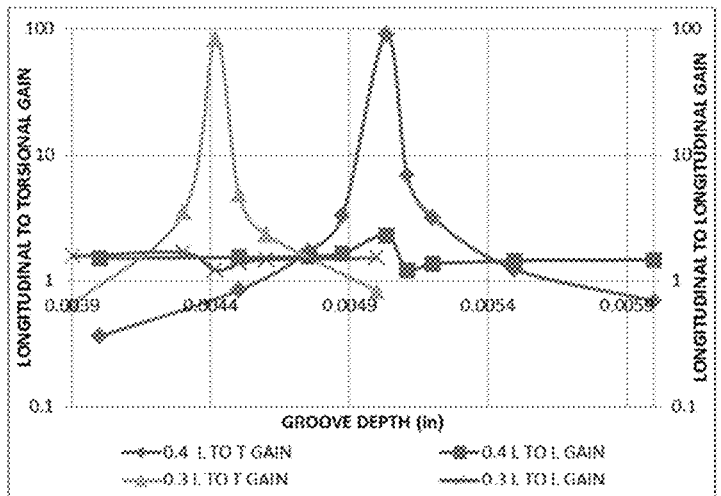
FIG. 12 is a graph similar to that of FIG. 9, wherein longitudinal to torsional gains and longitudinal to longitudinal gains for two needles having helical grooves of different axial lengths are plotted for comparison.
Figure 13:
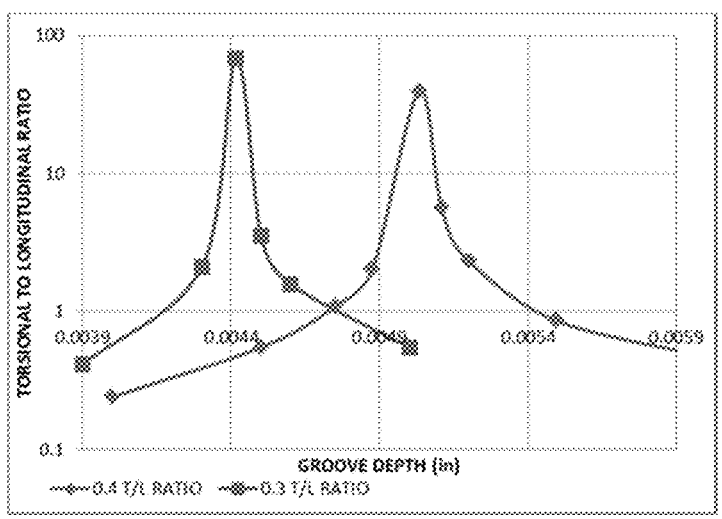
FIG. 13 is a graph similar to that of FIG. 10, wherein torsional to longitudinal ratios for two needles having helical grooves of different axial lengths are plotted for comparison.
Figure 14:
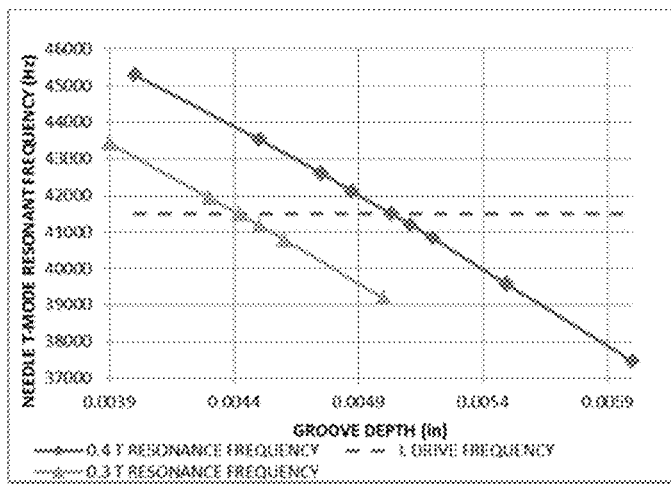
FIG. 14 is a graph similar to that of FIG. 11, wherein torsional mode frequencies for two needles having helical grooves of different axial lengths are plotted for comparison.

Additional simulations were performed to investigate the effect other groove parameters have upon the conversion of longitudinal motion at the needle base 12 to torsional motion at its tip 18. The groove length GL of the grooves 24 along the longitudinal axis 11 of needle shaft 16 was reduced from 0.4 inches to 0.3 inches. A series of simulations were performed for the reduced groove length and variations in the depth of the grooves. The groove width GW and helical pitch were unchanged at 0.011 inches and 0.8 inches, respectively, and the number of grooves remained at six. A drive frequency of 41.5 KHz was again chosen. FIG. 12 depicts the L-T gain and L-L gain versus groove depth for needle 10 with shortened grooves compared with results for the needle having grooves that are 0.4 inches long. FIG. 13 provides a similar comparison of T-L ratio at tip 18. FIG. 14 compares torsional resonant frequency results for the needles having different groove lengths. Respective peaks in L-T gain and T-L ratio occur at a shallower groove depth of roughly 0.0044" when shorter grooves are provided. The torsional mode resonances for the needle having shorter grooves are lower in frequency for the same groove depth when compared to the torsional mode resonances for the needle having longer grooves. While shortening the grooves in general decreases the torsional resonance frequency for a given groove depth, the peak in longitudinal to torsional amplification does not appear to change significantly.

Figure 15:
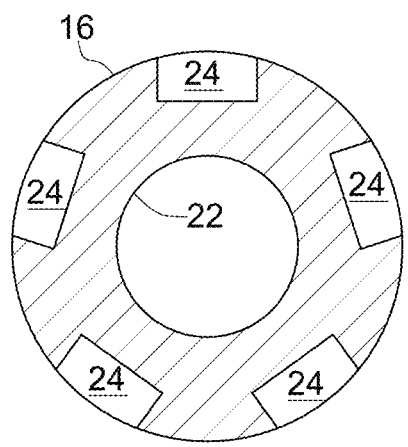
FIG. 15 is an enlarged cross-sectional view similar to that of FIG. 4, wherein a total number of helical grooves is reduced from six to five to provide further alternative groove configurations.
Figure 16:
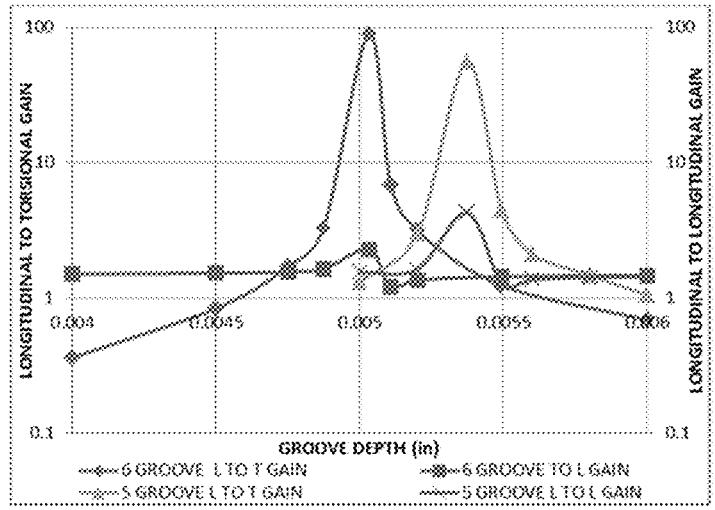
FIG. 16 is a graph similar to that of FIG. 9, wherein longitudinal to torsional gains and longitudinal to longitudinal gains for two needles having a different number of helical grooves are plotted for comparison.
Figure 17:
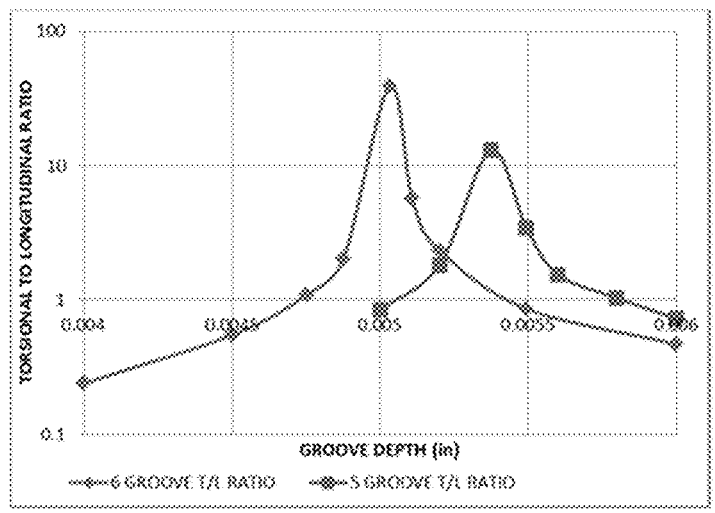
FIG. 17 is a graph similar to that of FIG. 10, wherein torsional to longitudinal ratios for two needles having a different number of helical grooves are plotted for comparison.

The final series of simulations was performed for a needle with five grooves instead of six, as illustrated in FIG. 15. Again the groove depth GD was varied, the groove width GW and helical pitch were unchanged at 0.011 inches and 0.8 inches, respectively, and a longitudinal drive frequency was set at 41.5 KHz. FIG. 16 depicts L-T gain and L-L gain for the five-groove needle compared to the six-groove needle. Variation in T-L ratio and torsional mode resonant frequency are plotted in FIGS. 17 and 18 for both the five-groove and six-groove needle designs.

Figure 18:
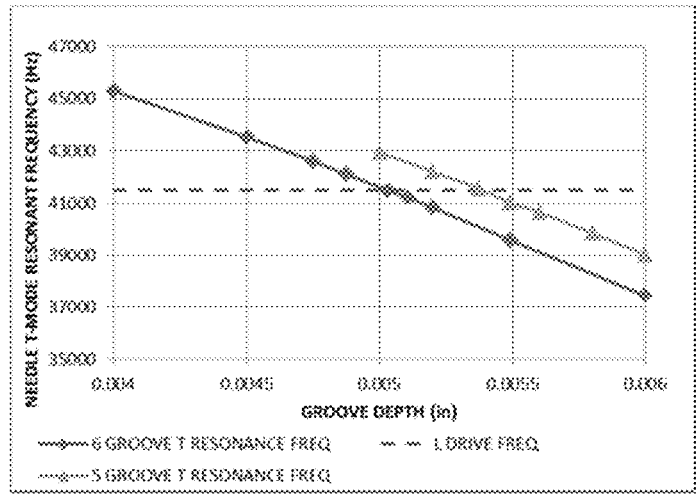
FIG. 18 is a graph similar to that of FIG. 11, wherein torsional mode frequencies for two needles having a different number of helical grooves are plotted for comparison.

Decreasing the number of grooves from six to five shifts the peak for L-T gain and T-L ratio to a deeper groove depth of about 0.0054 inches. The peak L-T gain achieved with the five-groove needle is less than that achieved with the six-groove needle, whereas the peak L-L gain achieved with the five-groove needle is greater than that achieved with the six-groove needle. These behaviors combine to significantly reduce the T-L ratio for the five-groove needle relative to the six-groove needle. FIG. 18 reveals that for a given groove depth GD, the torsional resonant mode frequency is greater for the five-groove needle than it is for the six-groove needle.

Simulations may be performed for other possible changes in the groove parameters. For example, the effect of varying the groove width GW may be investigated. In addition to the groove parameters, other needle features may be altered, including changes in the tip geometry. For example, tip 18 may be bent, which is known to convert torsion about axis 11 to amplified transverse motion at the edge of the tip. The tip 18 could also be flared. Flaring the tip amplifies torsional motion about axis 11 generating maximum shearing motion at both flared edges to improve cutting efficiency.

The simulations described herein are adequate to demonstrate the degree to which L-T gain, T-L ratio, and torsional mode frequency for needle 10 may be altered by controlling certain groove parameters, and that an L-T gain greater than one is achievable for ultrasonic phacoemulsification handpieces operated in a longitudinal mode. In each case the efficiency with which the handpiece system converts longitudinal motion at the end of the horn into torsional motion at the tip of the needle will depend upon the degree to which the torsional mode resonant frequency of the needle is tuned or matched to the operating drive frequency of the handpiece. The torsional mode resonant frequency of the needle may be readily tuned by varying the groove geometry including depth, length, and pitch, and/or by varying the number of grooves or changing the needle material.

A useful advantage of the grooved needle 10 disclosed herein is that it may be attached to a handpiece used for longitudinal mode cataract surgery, thereby converting the handpiece to one that may be used for torsional mode cataract surgery. In cases where the surgeon prefers to perform longitudinal mode cataract surgery, the grooved needle may be removed and replaced by a standard longitudinal mode needle. The invention provides the surgeon with the flexibility of performing surgeries of either mode using the same handpiece.

Another advantage of the present invention is that a variety of needles may be provided having different groove parameters for producing different tip motions, and a surgeon may select one of the needles having desired operating characteristics depending upon the surgical needs.

Grooved needle 10 may also be used with torsional mode handpieces of the prior art. Since the longitudinal motion generated by the handpiece stack is only partially converted to torsional motion in these torsional mode handpieces, the grooved needle 10 of the present invention may be used to further increase torsional motion at the needle tip to improve cataract cutting efficiency.

While helical grooves 24 are described for converting longitudinal motion to torsional motion, other non-linear groove paths may be used without straying from the invention.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the invention.

What is claimed is:

1. A phacoemulsification needle for attachment to an ultrasonic handpiece operable to drive the needle back-and-forth in opposite longitudinal directions of the needle at a longitudinal drive frequency and a longitudinal drive magnitude, the phacoemulsification needle comprising:
    a base adapted for removable attachment to the handpiece; and
    an elongated shaft extending from the base along a longitudinal axis, the shaft terminating at a distal tip having a cutting edge;
    the base and the shaft including an aspiration lumen passing therethrough;
    the shaft further including a plurality of external grooves extending in a longitudinal direction of the shaft;
    wherein the plurality of grooves have a configuration that converts oscillatory longitudinal drive motion applied at the base of the needle to torsional motion at the tip of the needle, the torsional motion having a fundamental torsional mode frequency and a torsional mode magnitude, wherein the torsional mode magnitude is greater than the longitudinal drive magnitude;
    wherein the plurality of grooves are helical grooves extending in the longitudinal direction of the shaft; and
    wherein i) the plurality of grooves consists of exactly six grooves each having a helical pitch less than or equal to 22.86 mm, or ii) each of the plurality of grooves has a depth in a range from 0.102 mm through 0.124 mm and an axial length of 7.62 mm or iii) each of the plurality of grooves has a depth in a range from 0.116 mm through 0.142 mm and an axial length of 10.16 mm, or iv) the plurality of grooves consists of exactly five grooves each having a depth in a range from 0.127 mm through 0.152 mm.

2. The phacoemulsification needle according to claim 1, wherein the plurality of grooves are configured such that the fundamental torsional mode frequency is the same as the longitudinal drive frequency.

3. The phacoemulsification needle according to claim 1, wherein the configuration of the plurality of grooves includes a helical pitch of the grooves, a width of the grooves, a depth of the grooves, an axial length of the grooves, and a total number of grooves.

4. A phacoemulsification system comprising:
    an ultrasonic handpiece operable to provide at least an oscillatory longitudinal drive motion having a longitudinal drive frequency and a longitudinal drive magnitude; and
    a needle removably attached to the handpiece, wherein the needle includes an elongated shaft having a plurality of external grooves extending in a longitudinal direction of the shaft, and wherein the needle terminates at a distal tip remote from where the needle is attached to the handpiece;
    wherein the plurality of grooves have a configuration that converts the longitudinal drive motion applied to the needle by the handpiece to torsional motion at the distal tip of the needle, the torsional motion having a fundamental torsional mode frequency and a torsional mode magnitude, wherein the torsional mode magnitude is greater than the longitudinal drive magnitude;
    wherein the plurality of grooves are helical grooves extending in the longitudinal direction of the shaft; and
    wherein i) the plurality of grooves consists of exactly six grooves each having a helical pitch less than or equal to 22.86 mm, or ii) each of the plurality of grooves has a depth in a range from 0.102 mm through 0.124 mm and an axial length of 7.62 mm or iii) each of the plurality of grooves has a depth in a range from 0.116 mm through 0.142 mm and an axial length of 10.16 mm, or iv) the plurality of grooves consists of exactly five grooves each having a depth in a range from 0.127 mm through 0.152 mm.

5. The phacoemulsification system according to claim 4, wherein the plurality of grooves are configured such that the fundamental torsional mode frequency is the same as the longitudinal drive frequency.

6. The phacoemulsification system according to claim 4, wherein the longitudinal drive frequency is in a range from 38 KHz to 44 KHz.

7. The phacoemulsification system according to claim 6, wherein the longitudinal drive frequency is 41.5 KHz.

8. The phacoemulsification system according to claim 6, wherein the longitudinal drive magnitude is 0.1 mm.

9. The phacoemulsification system according to claim 4, wherein the configuration of the plurality of grooves includes a helical pitch of the grooves, a width of the grooves, a depth of the grooves, an axial length of the grooves, and a total number of grooves.

10. The phacoemulsification system according to claim 4, wherein the ultrasonic handpiece is operable to provide a combined longitudinal and torsional drive motion.

\* \* \* \* \*